United States Patent
Keppel (10) Patent No.: US 7,255,694 B2
(45) Date of Patent: Aug. 14, 2007

(54) VARIABLE OUTPUT CREST FACTOR ELECTROSURGICAL GENERATOR

(75) Inventor: David S. Keppel, Longmont, CO (US)

(73) Assignee: Sherwood Services AG, Schaffausen (CH)

( * ) Notice: Subject to any disclaimer, the term of this patent is extended or adjusted under 35 U.S.C. 154(b) by 248 days.

(21) Appl. No.: 10/728,259

(22) Filed: Dec. 4, 2003

(65) Prior Publication Data

US 2004/0147918 A1    Jul. 29, 2004

Related U.S. Application Data

(60) Provisional application No. 60/432,391, filed on Dec. 10, 2002.

(51) Int. Cl.
   *A61B 18/18* (2006.01)
(52) U.S. Cl. .......................................... 606/34; 606/38
(58) Field of Classification Search ............. 606/32–42
   See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 2,982,881 A | 5/1961 | Reich |
| 3,058,470 A | 10/1962 | Seeliger et al. |
| 3,089,496 A | 5/1963 | Degelman |
| 3,163,165 A | 12/1964 | Islikawa |
| 3,252,052 A | 5/1966 | Nash |
| 3,391,351 A | 7/1968 | Trent |
| 3,402,326 A | 9/1968 | Guasco et al. |
| 3,413,480 A | 11/1968 | Biard et al. |

(Continued)

FOREIGN PATENT DOCUMENTS

DE    179607    3/1905

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83;(1995) pp. 271-276.

(Continued)

*Primary Examiner*—Michael Peffley (57) ABSTRACT

An electrosurgical generator is disclosed capable of controlling the output crest factor, as well as the output power of the electrosurgical generator across a range of tissue impedances during electrosurgery. The control occurs automatically, in real time and continuously during the duration of electrosurgical activation of the electrosurgical generator by varying both the output crest factor and output power based on the changing impedance of the tissue. The electrosurgical generator also includes controls for allowing a surgeon to manually select the appropriate crest factor value and power output value for a particular surgical procedure. By automatically adjusting the output crest factor and by giving the surgeon the ability to manually "tailor" the output crest factor across a range of tissue impedance, the electrosurgical generator enhances the ultimate surgical effect and desirable surgical results.

18 Claims, 2 Drawing Sheets

U.S. PATENT DOCUMENTS

| | | |
|---|---|---|
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A * | 3/1980 | Belt et al. ...................... 606/37 |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |
| 4,862,889 A | 9/1989 | Feucht |
| 4,880,719 A | 11/1989 | Murofushi et al. |

| Patent | Date | Inventor |
|---|---|---|
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A * | 10/1990 | Carder ........................ 323/322 |
| 4,961,435 A | 10/1990 | Kitagawa et al. |
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,015,227 A | 5/1991 | Broadwin et al. |
| 5,019,176 A | 5/1991 | Brandhorst, Jr. |
| 5,029,588 A | 7/1991 | Yock et al. |
| 5,087,257 A | 2/1992 | Farin |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,162,217 A | 11/1992 | Hartman |
| 5,167,658 A | 12/1992 | Ensslin |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,249,121 A | 9/1993 | Baum et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,300,068 A | 4/1994 | Rosar et al. |
| 5,300,070 A | 4/1994 | Gentelia |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,396,062 A | 3/1995 | Eisentraut et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,006 A | 4/1995 | Buchholtz et al. |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,430,434 A | 7/1995 | Lederer et al. |
| 5,432,459 A | 7/1995 | Thompson |
| 5,433,739 A | 7/1995 | Sluijter et al. |
| 5,434,398 A | 7/1995 | Goldberg |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,478,303 A | 12/1995 | Folry-Nolan et al. |
| 5,480,399 A | 1/1996 | Hebborn |
| 5,483,952 A | 1/1996 | Aranyi |
| 5,485,312 A | 1/1996 | Horner et al. |
| 5,490,850 A | 2/1996 | Ellman et al. |
| 5,496,312 A | 3/1996 | Klicek |
| 5,496,313 A | 3/1996 | Gentelia et al. |
| 5,500,012 A | 3/1996 | Brucker et al. |
| 5,500,616 A | 3/1996 | Ochi |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,681 A | 7/1996 | Strul et al. |
| 5,540,683 A | 7/1996 | Ichikawa |
| 5,540,684 A | 7/1996 | Hassler, Jr. |
| 5,540,724 A | 7/1996 | Cox |
| 5,556,396 A | 9/1996 | Cohen et al. |
| 5,558,671 A | 9/1996 | Yates |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,594,636 A | 1/1997 | Schauder |
| 5,596,466 A | 1/1997 | Ochi |
| 5,599,344 A | 2/1997 | Paterson |
| 5,599,345 A | 2/1997 | Edwards et al. |
| 5,605,150 A | 2/1997 | Radons et al. |
| 5,613,966 A | 3/1997 | Makower et al. |
| 5,613,996 A | 3/1997 | Lindsay |
| 5,625,370 A | 4/1997 | D'Hont |
| 5,626,575 A | 5/1997 | Crenner |
| 5,628,745 A | 5/1997 | Bek |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,688,267 A | 11/1997 | Panescu et al. |
| 5,690,692 A | 11/1997 | Fleming |
| 5,693,042 A | 12/1997 | Bioarski et al. |
| 5,694,304 A | 12/1997 | Telefus et al. |
| 5,695,494 A | 12/1997 | Becker |
| 5,696,351 A | 12/1997 | Benn et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,720,744 A | 2/1998 | Eggleston et al. |
| 5,722,975 A | 3/1998 | Edwards et al. |
| 5,733,281 A | 3/1998 | Nardella |
| 5,749,869 A | 5/1998 | Lindenmeier et al. |
| 5,749,871 A | 5/1998 | Hood et al. |

| Patent No. | Date | Inventor |
|---|---|---|
| 5,755,715 A | 5/1998 | Stern |
| 5,766,165 A | 6/1998 | Gentelia et al. |
| 5,769,847 A | 6/1998 | Panescu |
| 5,772,659 A | 6/1998 | Becker et al. |
| 5,792,138 A | 8/1998 | Shipp |
| 5,797,802 A | 8/1998 | Nowak |
| 5,797,902 A | 8/1998 | Netherly |
| 5,814,092 A | 9/1998 | King |
| 5,817,093 A | 10/1998 | Williamson, IV et al. |
| 5,820,568 A | 10/1998 | Willis |
| 5,827,271 A | 10/1998 | Bussey et al. |
| 5,830,212 A | 11/1998 | Cartmell |
| 5,836,943 A | 11/1998 | Miller, III |
| 5,836,990 A | 11/1998 | Li |
| 5,846,236 A | 12/1998 | Lindenmeier et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,897,552 A | 4/1999 | Edwards et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,948,007 A | 9/1999 | Starkenbaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,961,344 A | 10/1999 | Rosales et al. |
| 5,971,980 A | 10/1999 | Sherman |
| 5,976,128 A | 11/1999 | Schilling et al. |
| 5,983,141 A | 11/1999 | Sluijter et al. |
| 6,010,499 A | 1/2000 | Cobb |
| 6,014,581 A | 1/2000 | Whayne et al. |
| 6,033,399 A * | 3/2000 | Gines ............ 606/38 |
| 6,044,283 A | 3/2000 | Fein et al. |
| 6,053,910 A | 4/2000 | Fleenor |
| 6,053,912 A | 4/2000 | Panescu et al. |
| 6,056,745 A | 5/2000 | Panescu et al. |
| 6,056,746 A | 5/2000 | Goble et al. |
| 6,063,075 A | 5/2000 | Mihori |
| 6,063,078 A | 5/2000 | Wittkampf |
| 6,068,627 A | 5/2000 | Orszulak et al. |
| 6,074,386 A | 6/2000 | Goble et al. |
| 6,093,186 A | 7/2000 | Goble |
| RE36,871 E | 9/2000 | Epstein |
| 6,113,591 A | 9/2000 | Whayne et al. |
| 6,113,596 A | 9/2000 | Hooven |
| 6,123,702 A | 9/2000 | Swanson et al. |
| 6,132,429 A | 10/2000 | Baker |
| 6,142,992 A | 11/2000 | Cheng et al. |
| 6,162,217 A | 12/2000 | Kannenberg et al. |
| 6,171,304 B1 | 1/2001 | Netherly et al. |
| 6,203,541 B1 | 3/2001 | Keppel |
| 6,210,403 B1 | 4/2001 | Klicek |
| 6,228,080 B1 | 5/2001 | Gines |
| 6,228,081 B1 | 5/2001 | Goble |
| 6,231,569 B1 | 5/2001 | Bek |
| 6,238,387 B1 | 5/2001 | Miller, III |
| 6,238,388 B1 | 5/2001 | Ellman |
| 6,241,725 B1 | 6/2001 | Cosman |
| 6,245,065 B1 | 6/2001 | Panescu |
| 6,246,912 B1 | 6/2001 | Sluijter et al. |
| 6,251,106 B1 | 6/2001 | Becker et al. |
| 6,258,085 B1 | 7/2001 | Eggleston |
| 6,261,285 B1 | 7/2001 | Novak |
| 6,273,886 B1 | 8/2001 | Edwards |
| 6,275,786 B1 | 8/2001 | Daners |
| 6,293,941 B1 | 9/2001 | Strul |
| 6,306,131 B1 | 10/2001 | Hareyama et al. |
| 6,306,134 B1 | 10/2001 | Goble et al. |
| 6,309,386 B1 | 10/2001 | Bek |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,383,183 B1 | 5/2002 | Sekino et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,743 B1 | 6/2002 | Orszulak et al. |
| 6,436,096 B1 | 8/2002 | Hareyama |
| 6,451,015 B1 | 9/2002 | Rittman, III et al. |
| 6,458,121 B1 | 10/2002 | Rosenstock |
| 6,464,689 B1 | 10/2002 | Qin |
| 6,464,696 B1 | 10/2002 | Oyama |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside et al. |
| 6,524,308 B1 | 2/2003 | Muller et al. |
| 6,547,786 B1 | 4/2003 | Goble |
| 6,562,037 B2 | 5/2003 | Paton |
| 6,565,559 B2 | 5/2003 | Eggleston |
| 6,573,248 B2 | 6/2003 | Ramasamy et al. |
| 6,575,969 B1 | 6/2003 | Rittman, III et al. |
| 6,620,157 B1 | 9/2003 | Dabney et al. |
| 6,623,423 B2 | 9/2003 | Sakurai |
| 6,635,057 B2 | 10/2003 | Harano |
| 6,648,883 B2 | 11/2003 | Francischelli |
| 6,652,514 B2 | 11/2003 | Ellman |
| 6,663,623 B1 * | 12/2003 | Oyama et al. ............ 606/38 |
| 6,663,624 B2 | 12/2003 | Edwards |
| 6,666,860 B1 | 12/2003 | Takahashi |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,692,489 B1 | 2/2004 | Heim |
| 6,712,813 B2 | 3/2004 | Ellman |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,783,523 B2 | 8/2004 | Qin |
| 6,790,206 B2 | 9/2004 | Panescu |
| 6,796,981 B2 | 9/2004 | Wham |
| 6,824,539 B2 | 11/2004 | Novak |
| 6,830,569 B2 | 12/2004 | Thompson |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,893,435 B2 | 5/2005 | Roane |
| 7,044,948 B2 | 5/2006 | Keppel |
| 7,060,063 B2 | 6/2006 | Marion et al. |
| 7,063,692 B2 | 6/2006 | Sakurai et al. |
| 7,066,933 B2 | 6/2006 | Hagg |
| 7,131,860 B2 | 11/2006 | Sartor et al. |
| 7,137,980 B2 | 11/2006 | Buysse et al. |
| 2001/0014804 A1 | 8/2001 | Goble et al. |
| 2001/0031962 A1 | 10/2001 | Eggleston |
| 2002/0035353 A1 | 3/2002 | Edwards et al. |
| 2002/0035364 A1 | 3/2002 | Schoenman et al. |
| 2002/0068932 A1 | 6/2002 | Edwards |
| 2002/0107517 A1 | 8/2002 | Witt et al. |
| 2002/0111624 A1 | 8/2002 | Witt et al. |

| | | | | | | |
|---|---|---|---|---|---|---|
| 2002/0193787 | A1 | 12/2002 | Qin | DE | 3904558 | 8/1990 |
| 2003/0004510 | A1 | 1/2003 | Wham et al. | DE | 3942998 | 7/1991 |
| 2003/0060818 | A1 | 3/2003 | Kannenberg | DE | 4339049 A1 | 5/1995 |
| 2003/0078572 | A1 | 4/2003 | Pearson et al. | DE | 19717411 | 11/1998 |
| 2003/0139741 | A1 | 7/2003 | Goble et al. | DE | 19848540 A1 | 5/2000 |
| 2003/0153908 | A1 | 8/2003 | Goble | EP | 246350 | 11/1987 |
| 2003/0163123 | A1 | 8/2003 | Goble | EP | 310431 | 4/1989 |
| 2003/0163124 | A1 | 8/2003 | Goble | EP | 325456 | 7/1989 |
| 2003/0171745 | A1 | 9/2003 | Francischelli | EP | 336742 | 10/1989 |
| 2003/0199863 | A1 | 10/2003 | Swanson | EP | 390937 | 10/1990 |
| 2003/0225401 | A1 | 12/2003 | Eggers et al. | EP | 556705 | 8/1993 |
| 2004/0001521 | A1 | 1/2004 | DeSisto | EP | 0569130 A1 | 11/1993 |
| 2004/0002745 | A1 | 1/2004 | Flemming | EP | 608609 | 8/1994 |
| 2004/0019347 | A1 | 1/2004 | Sakurai | EP | 836868 | 4/1998 |
| 2004/0024395 | A1 | 2/2004 | Ellman | EP | 878169 | 11/1998 |
| 2004/0030328 | A1 | 2/2004 | Eggers | EP | 1293171 | 3/2003 |
| 2004/0030330 | A1 | 2/2004 | Brassell et al. | EP | 0880220 B1 | 6/2006 |
| 2004/0044339 | A1 | 3/2004 | Beller | FR | 1275415 | 10/1961 |
| 2004/0049179 | A1 | 3/2004 | Francischelli | FR | 1347865 | 11/1963 |
| 2004/0054365 | A1 | 3/2004 | Goble | FR | 2313708 | 12/1976 |
| 2004/0068304 | A1 | 4/2004 | Paton | FR | 2502935 | 10/1982 |
| 2004/0082946 | A1 | 4/2004 | Malis | FR | 2517953 | 6/1983 |
| 2004/0095100 | A1 | 5/2004 | Thompson | FR | 2573301 | 5/1986 |
| 2004/0097912 | A1 | 5/2004 | Gonnering | GB | 607850 | 9/1948 |
| 2004/0097914 | A1 | 5/2004 | Pantera | GB | 855459 | 11/1960 |
| 2004/0097915 | A1 | 5/2004 | Refior | GB | 902775 | 8/1962 |
| 2004/0116919 | A1 | 6/2004 | Heim | GB | 2164473 | 3/1986 |
| 2004/0133189 | A1 | 7/2004 | Sakurai | GB | 2214430 | 9/1989 |
| 2004/0138653 | A1 | 7/2004 | Dabney | GB | 2358934 A | 8/2001 |
| 2004/0138654 | A1 | 7/2004 | Goble | SU | 166452 | 1/1965 |
| 2004/0172016 | A1 | 9/2004 | Bek | SU | 727201 | 4/1980 |
| 2004/0230189 | A1 | 11/2004 | Keppel | WO | WO92/06642 | 4/1992 |
| 2004/0243120 | A1 | 12/2004 | Orszulak et al. | WO | WO93/24066 | 12/1993 |
| 2004/0260279 | A1 | 12/2004 | Goble | WO | WO94/24949 | 11/1994 |
| 2005/0004564 | A1 | 1/2005 | Wham | WO | WO94/28809 | 12/1994 |
| 2005/0004569 | A1 | 1/2005 | Witt et al. | WO | WO95/09577 | 4/1995 |
| 2005/0021022 | A1 | 1/2005 | Sturm et al. | WO | WO95/19148 | 7/1995 |
| 2005/0101951 | A1 | 5/2005 | Wham | WO | WO96/02180 | 2/1996 |
| 2005/0113818 | A1 | 5/2005 | Sartor | WO | WO96/04860 | 2/1996 |
| 2005/0113819 | A1 | 5/2005 | Wham | WO | WO96/08794 | 3/1996 |
| 2005/0149151 | A1 | 7/2005 | Orszulak | WO | WO96/18349 | 6/1996 |
| 2005/0182398 | A1 | 8/2005 | Paterson | WO | WO96/29946 | 10/1996 |
| 2005/0197659 | A1 | 9/2005 | Bahney | WO | WO96/39914 | 12/1996 |
| 2005/0203504 | A1 | 9/2005 | Wham et al. | WO | WO97/06739 | 2/1997 |
| 2006/0025760 | A1 | 2/2006 | Podhajsky | WO | WO97/06740 | 2/1997 |
| 2006/0079871 | A1 | 4/2006 | Plaven et al. | WO | WO97/06855 | 2/1997 |
| 2006/0161148 | A1 | 7/2006 | Behnke | WO | WO97/17029 | 5/1997 |
| 2006/0178664 | A1 | 8/2006 | Keppel | WO | WO02/11634 | 2/2002 |
| 2006/0224152 | A1 | 10/2006 | Behnke et al. | WO | WO02/45589 | 6/2002 |
| 2006/0281360 | A1 | 12/2006 | Sartor et al. | WO | WO02/47565 | 6/2002 |
| | | | | WO | WO 0247565 | 6/2002 |
| | | | | WO | WO02/088128 | 7/2002 |
| | | | | WO | WO 03/092520 | 11/2003 |
| | | | | WO | WO 2005/060365 | 11/2003 |
| | | | | WO | WO 2004/028385 | 4/2004 |
| | | | | WO | WO 2004/098385 | 4/2004 |
| | | | | WO | WO 2005/046496 | 5/2005 |
| | | | | WO | WO 2005/048809 | 6/2005 |
| | | | | WO | WO 2005/050151 | 6/2005 |
| | | | | WO | WO05048809 A1 | 6/2005 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.

Astrahan, "A Localized Current Field Hyperthermia System for Use with 192-Iridium Interstitial Implants" Medical Physics, 9 (3), May/Jun. 1982.

Bergdahl et al., "Studies on Coagulation and the Development of an Automatic computerized Bioplar Coagulator" Journal of Neurosurgery 75:1, (Jul. 1991) pp. 148-151.

Cosman et al., "Methods of Making Nervous System Lesions" In William RH, Rengachary SS (eds): Neurosurgery, New York: McGraw-Hill, vol. 111, (1984), pp. 2490-2499.

Cosman et al., "Radiofrequency Lesion Generation and Its Effect on Tissue Impedance" Applied Neurophysiology 51: (1988) pp. 230-242.

Cosman et al., "Theoretical Aspects of Radiofrequency Lesions in the Dorsal Root Entry Zone" Neurosurgery 15:(1984) pp. 945-950.

Geddes et al., "The Measurement of Physiologic Events by Electrical Impedence" Am. J. MI; Jan. Mar. 1964, pp. 16-27.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure "The O.R. Pro 300" 1 p.

Sugita et al., "Bipolar Coagulator with Automatic Thermocontrol" J. Neurosurg., vol. 41, Dec. 1944, pp. 777-779.

Valleylab Brochure "Valleylab Electroshield Monitoring System" 2 pp.

Vallfors et al., "Automatically Controlled Bipolar Electrosoagulation-'COA-COMP'" Neurosurgical Review 7:2-3 (1984) pp. 187-190.

Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp.

Chicharo et al. "A Sliding Goertzel Algorith" Aug. 1996, pp. 283-297 Signal Processing, Elsevier Science Publishers B.V. Amsterdam, NL. vol. 52 No. 3.

Ogden "Goertzel Alternative to the Fourier Transform" Jun. 1993 pp. 485-487 Electronics World; Reed Business Publishing, Sutton, Surrey, GB vol. 99, No. 1687.

Medtrex Brochure "The O.R. Pro 300" 1 p. Sep. 1998.

Valleylab Brochure "Valleylab Electroshield Monitoring System" 2 pp. Nov. 1995.

Richard Wolf Medical Instruments Corp. Brochure, "Kleppinger Bipolar Forceps & Bipolar Generator" 3 pp. Jan. 1989.

Bergdahl et al. "Studies on Coagulation and the Development of an Automatic Computerized Bipolar Coagulator" J. Neurosurg, vol. 75, Jul. 1991, pp. 148-151.

International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report-PCT/US03/37110.
International Search Report-PCT/US03/37310.
International Search Report-EP4009964.
International Search Report-EP98300964.8.
International Search Report-EP04015981.6.

Ogden Goertzel Alternative to the Fourier Transform: Jun. 1993 pp. 485-487 Electronics World; Reed Business Publishing, Sutton, Surrey, BG vol. 99, No. 9, 1687.

International Search Report EP 06000708.5 dated Apr. 21, 2006.
International Search Report-Extended EP 06000708.5 dated Aug. 22, 2006.
International Search Report EP 05002769.7 dated Jun. 9, 2006.
International Search Report EP 06006717.0 dated Aug. 7, 2006.

Ni W et al: "A Signal Processing Method for the Coriolis Mass Flowmeter Based on a Normalized . . ." Journal of Applied Sciences-Yingyong Kexue Xuebao, Shanghai CN, vol. 23 No. 2;(Mar. 2005); 160-164.

* cited by examiner

VARIABLE OUTPUT CREST FACTOR ELECTROSURGICAL GENERATOR

CROSS REFERENCE TO RELATED APPLICATIONS

This application claims the benefit of priority to U.S. Provisional Application Ser. No. 60/432,391 filed on Dec. 10, 2002 the entire contents of which are hereby incorporated by reference herein.

BACKGROUND

1. Technical Field

The present disclosure is directed to electrosurgery and, in particular, to an electrosurgical generator capable of controlling its output crest factor, as well as the output power, across a range of tissue impedances during electrosurgery.

2. Description of the Related Art

Tissue heating is proportional to the square of the amount of current being generated through the tissue and tissue vaporization is, in turn, generally proportional to current. Vaporization of tissue is proportional to the amount of energy in an arc. This energy in combination with the Cathode Fall Voltage, derives the power of vaporization. Thermal spread is dependent on the amount of heat generated within the tissue which is dependent on tissue resistivity and the arc energy squared. As can be appreciated, by not controlling the thermal spread the depth of ablation is difficult to predict and control.

Therefore, during electrosurgery, an increase or decrease in the amount of current provides a different tissue effect. This phenomenon is due to a variable referred to as the crest factor (CF). The crest factor can be calculated using the formula: $CF = V_{PEAK}/V_{RMS}$, where $V_{PEAK}$ is the positive peak of the waveform and $V_{RMS}$ is the RMS value of the waveform. The crest factor can also be calculated using the formula: $CF = [(1-D)/D]^{1/2}$, where D is the duty cycle of the waveform and is defined as $D = T_1/(T_1 + T_2)$.

Based on the above formulas, it is evident that when operating an electrosurgical generator in either the "cut", "blend" or "coagulate" mode, the range of the crest factor varies from one mode to another. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. For the purposes herein, "coagulation" is defined as a process of desiccating tissue wherein the tissue cells are ruptured and dried. "Vessel sealing" is defined as the process of liquefying the collagen in the tissue so that it reforms into a fused mass with significantly-reduced demarcation between the opposing tissue structures (opposing walls of the lumen). Coagulation of small vessels is usually sufficient to permanently close them. Larger vessels need to be sealed to assure permanent closure.

An increase in the crest factor results in more current per arc at a given power setting. Further, since tissue heating is proportional to the amount of current through the tissue squared and tissue vaporization is proportional to the amount of current being generated through the tissue, a doubling of current per arc results in four times as much tissue heating and twice the amount of tissue vaporization.

Known electrosurgical generators do not control the crest factor of the electrosurgical output current. Such electrosurgical generators produce the same crest factor waveform across a range of tissue impedance. Some electrosurgical generators reduce or otherwise change the output power to achieve a surgical effect. However, no known electrosurgical generators alter both the output crest factor and output power across a range of tissue impedance to achieve a particular surgical effect. Accordingly, such electrosurgical generators do not have the ability to manipulate or control the proportion of tissue vaporization to tissue heating, in order to achieve more controllable and desirable surgical effects.

Therefore, it is an aspect of the present disclosure to provide an electrosurgical generator capable of regulating the output crest factor of the electrosurgical generator, as well as the output power, across a range of tissue impedance for controlling both tissue heating and tissue vaporization.

SUMMARY

An electrosurgical generator is disclosed capable of controlling its output crest factor, as well as the output power, across a range of tissue impedance during electrosurgery. The control occurs in real time during an electrosurgical procedure by the electrosurgical generator varying both the output crest factor and output power based on the changing impedance of the tissue.

The electrosurgical generator determines whether to vary the output crest factor and output power by monitoring the output voltage and output current. By monitoring the output voltage and output current, the electrosurgical generator, using programmable instructions executed by at least one processor, is able to determine the tissue impedance.

If the determined tissue impedance is low, the present value of the crest factor is low, and if the determined tissue impedance is high, the present value of the crest factor is high. According to the type of surgical procedure being performed, the electrosurgical generator then automatically adjusts or maintains the values of the output crest factor and the output power. The value of the output crest factor is preferably adjusted by varying the duty cycle of the generated waveform, the positive peak and/or RMS value of the generated waveform.

The electrosurgical generator also includes controls for allowing a surgeon to select the appropriate crest factor value and output power value for a particular surgical procedure. Hence, the output crest factor and output power can be manually adjusted by the inventive electrosurgical generator. Therefore, by automatically adjusting the output crest factor and by giving the surgeon the ability to manually "tailor" the output crest factor across a range of tissue impedance, the inventive electrosurgical generator allows for a greater range of surgical effect and desirable surgical results.

In brief, the electrosurgical generator of the present disclosure is capable of varying both the output crest factor and output power based on the changing impedance of tissue during electrosurgery. The electrosurgical generator includes a processing unit for receiving at least one signal indicative of an output voltage and an output current. The processing unit executes a set of programmable instructions for determining the tissue impedance using the output voltage and output current. The processing unit then transmits a waveform adjustment signal to a waveform generator which adjusts the output crest factor and output power based on the determined tissue impedance.

The method of the present disclosure varies both the output crest factor and output power of an electrosurgical generator based on the changing impedance of tissue during electrosurgery. The method includes the steps of determining tissue impedance using an output voltage and an output current of the electrosurgical generator. The method then includes the step of adjusting the output crest factor and output power of the electrosurgical generator based on the determined tissue impedance.

The present disclosure also provides a power source for generating an output voltage and an output current for an electrosurgical generator system which is capable of varying both the output crest factor and output power based on the changing impedance of tissue during electrosurgery. The electrosurgical system includes a processing unit for receiving at least one signal indicative of the output voltage and the output current. The processing unit executes a set of programmable instructions for determining the tissue impedance using the output voltage and output current and transmitting at least one waveform adjustment signal. The waveform adjustment signal is received by a waveform generator of the electrosurgical generator system for adjusting the output crest factor and output power based on the determined tissue impedance.

Further features of the above embodiments will become more readily apparent to those skilled in the art from the following detailed description of the apparatus taken in conjunction with the drawings.

BRIEF DESCRIPTION OF THE DRAWINGS

Various embodiments will be described herein below with reference to the drawings wherein.

DETAILED DESCRIPTION

Figure 1:
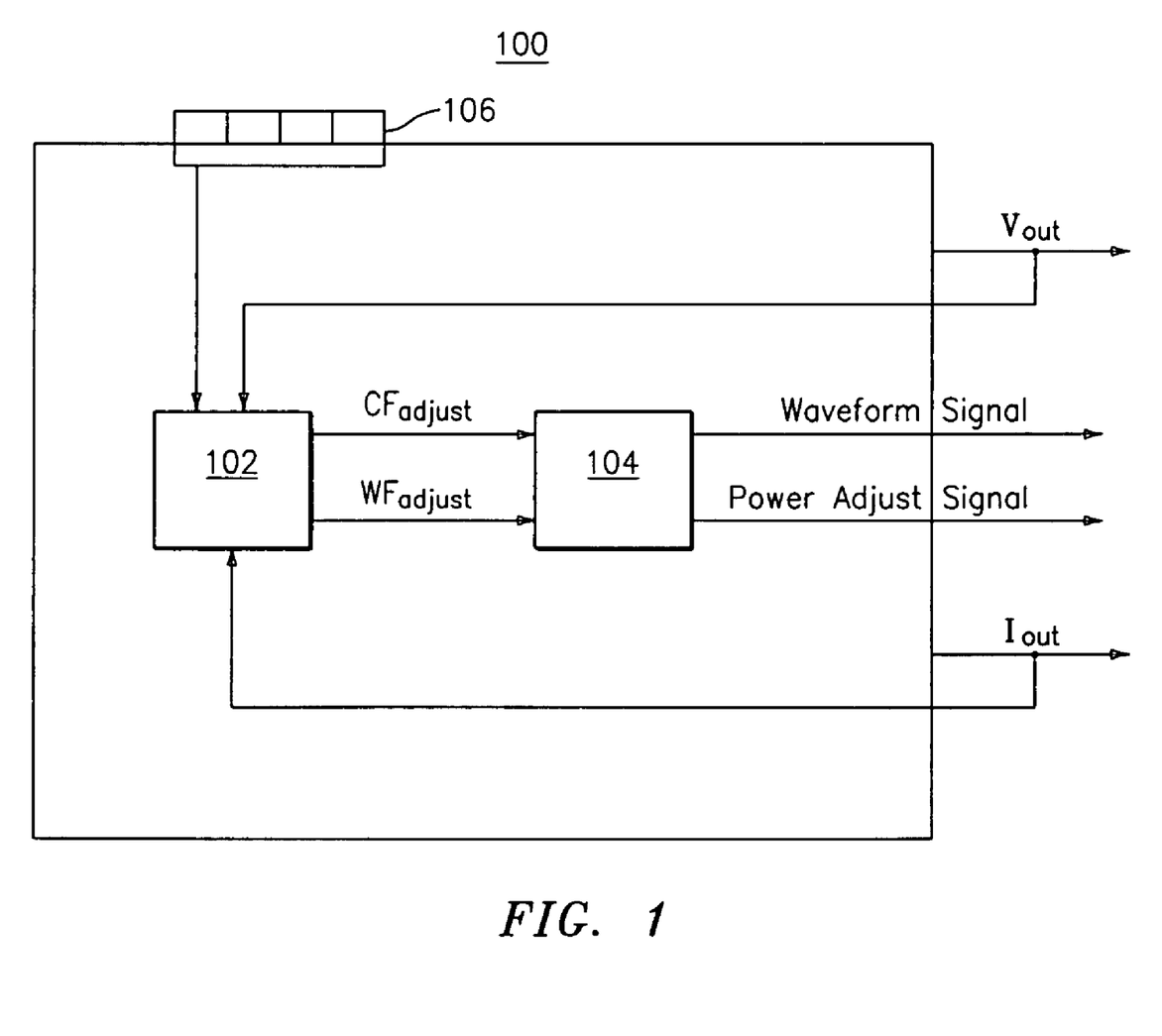
FIG. 1 is a schematic diagram of an electrosurgical generator in accordance with one embodiment.

Reference should be made to the drawings where like reference numerals refer to similar elements. Referring to FIG. 1, there is shown a schematic diagram of one embodiment of the present electrosurgical generator. The electrosurgical generator is designated generally by reference numeral 100 and it includes a processor 102 for receiving voltage and current output signals, $V_{out}$ and $I_{out}$, for monitoring the output voltage and output current, respectively. Using the signals $V_{out}$ and $I_{out}$, the processor 102 calculates the tissue impedance using a set of programmable instructions.

After calculating the tissue impedance, the processor 102 accesses at least one look-up table or other data structure to determine an appropriate output crest factor value and output power value for the calculated tissue impedance. The look-up table or other data structure is stored within a memory module of the processor 102 or, alternatively, within an external memory. (Not shown.) After determining the proper output crest factor value and output power value for the calculated tissue impedance, the processor 102 determines whether to adjust the output crest factor and/or the output power to predetermined values, i.e., the values provided by the look-up table.

The processor 102 adjusts the output crest factor by sending a signal $CF_{adjust}$ to a waveform generator 104 to alter the duty cycle of the generated waveform or waveform signal. By altering the duty cycle of the generated waveform, the output crest factor is adjusted in accordance with the following formula: $CF=[(1-D)/D]^{1/2}$, where D is the duty cycle of the waveform and is defined as $D=T_1/(T_1+T_2)$.

The processor 102 can also adjust the output crest factor by sending a signal $WF_{adjust}$ to the waveform generator 104 to alter the positive peak and/or RMS value of the generated waveform in accordance with the following formula: $CF=V_{PEAK}/V_{RMS}$, where $V_{PEAK}$ is the positive peak of the waveform and $V_{RMS}$ is the RMS value of the waveform. The two signals $CF_{adjust}$ and $WF_{adjust}$ may be generated and sent by the processor 102 to the waveform generator 104 simultaneously or sequentially as determined by a set of programmable instructions executed by the processor 102.

Preferably, the processor 102 determines which of the parameters to alter, i.e., the duty cycle, the positive peak of the generated waveform and/or the RMS value of the generated waveform according to which parameter change would provide the most desirable and/or particular surgical result. Hence, the processor 102 takes into consideration which surgical procedure is being performed, (i.e., which operational mode is currently activated on the electrosurgical generator 100-cut, coagulate, blend or seal) prior to altering the output crest factor. The processor 102 adjusts the output power by adjusting the output voltage $V_{out}$ and/or output current out as known in the art.

The adjustment of the output crest factor and output power as described above occurs automatically, in real time and continuously for the duration of the surgical procedure. That is, during the activation of the electrosurgical generator 100, it is envisioned that the electrosurgical generator 100 can vary the output crest factor, output power output and/or the waveform based on the changing impedance of the tissue as determined by continuously monitoring the output voltage $V_{out}$ and output current $I_{out}$.

Figure 2:
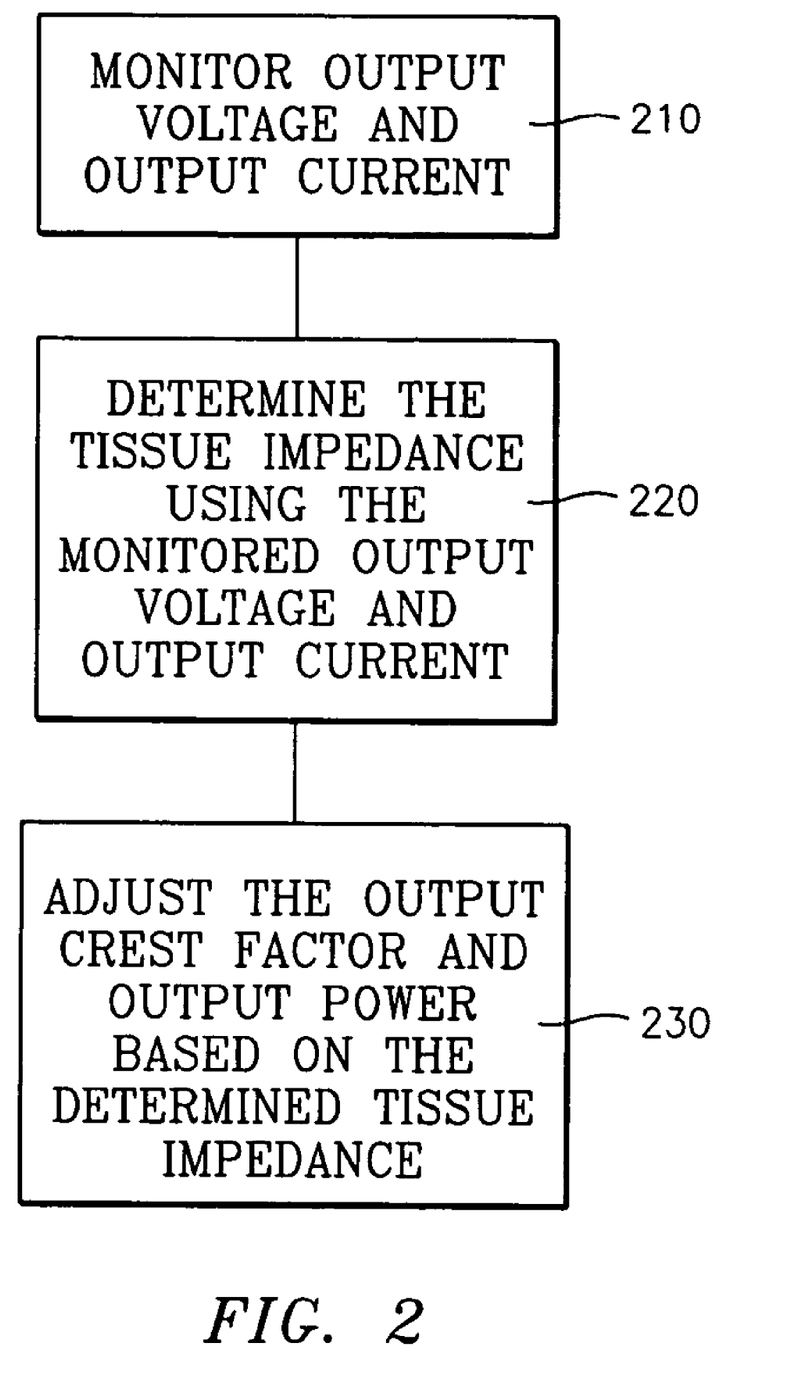
FIG. 2 is a flowchart illustrating a method of operation of the electrosurgical generator in accordance with the present disclosure.

FIG. 2 shows a flow chart illustrating a method for controlling the electrosurgical generator 100 in accordance with the present disclosure. In step 210, the method includes monitoring the output voltage $V_{out}$ and output current $I_{out}$ of the electrosurgical generator 100. In step 220, the tissue impedance is determined using the monitored output voltage and output current. In step 230, the output crest factor and output power of the electrosurgical generator are adjusted based on the determined tissue impedance.

A surgeon may override the method described above and illustrated by the flow chart of FIG. 2 by selectively adjusting controls 106 on the electrosurgical generator 100 to a particular output crest factor value and/or output power value for achieving a particular surgical effect. By adjusting the controls 106, the processor 102 sends a signal to the waveform generator 104 to alter the duty cycle of the generated waveform, or other parameter, such that the output crest factor is approximately equal to the output crest factor selected by the surgeon.

The controls 106 afford the surgeon the opportunity to manually "tailor" the mode for the surgical procedure. For example, during the "cut" operational mode, the processor 102 using the set of programmable instructions would adjust the output crest factor to be within the range of 1.4 to 2.0. However, the surgeon may determine that the type of tissue being cut requires the generated waveform to have an output crest factor value of 1.1 or less. Hence, the surgeon can override the automatic and real time adjustment of the output crest factor value by manually setting the output crest factor value to 1.1 using the controls 106. In addition, the surgeon may wish to control the power for other reasons, e.g., limit the thermal spread to surrounding tissue.

Examples and benefits to controlling the power are explained in detail in commonly-assigned U.S. Pat. No. 6,228,080, the entire contents of which are hereby incorporated by reference herein.

It is contemplated that the electrosurgical generator 100 can be designed to determine the tissue impedance and adjust the output crest factor and the output power accordingly by utilizing circuitry and other hardware, rather than using programmable instructions executed by the processor 102.

Accordingly, the present disclosure provides an electrosurgical generator 100 which is capable of controlling both the output crest factor and output power across a range of tissue impedance during electrosurgery.

Although this disclosure has been described with respect to preferred embodiments, it will be readily apparent to those having ordinary skill in the art to which it appertains that changes and modifications may be made thereto without departing from the spirit or scope of the disclosure.

What is claimed is:

1. An electrosurgical generator capable of varying both the output crest factor and output power of at least one waveform based on the changing impedance of tissue during electrosurgery, said electrosurgical generator comprising:
   a processing unit for receiving at least one signal indicative of an output voltage and an output current of the at least one waveform, said processing unit executing a set of programmable instructions for determining the tissue impedance using the output voltage and output current of the at least one waveform and transmitting at least one waveform adjustment signal; and
   a waveform generator for receiving the at least one waveform adjustment signal which alters the duty cycle of the at least one waveform to adjust the output crest factor and output power of the at least one waveform based on the determined tissue impedance, wherein said at least one waveform adjustment signal includes data to alter the duty cycle of the at least one waveform generated by the waveform generator in accordance with the following formula: $CF=[(1-D)/D]^{1/2}$, wherein D is the duty cycle and CF is the crest factor of the generated waveform.

2. An electrosurgical generator as in claim 1, wherein said processing unit further determines a corresponding output crest factor value and output power value of the at least one waveform for the determined tissue impedance by accessing at least one data structure.

3. An electrosurgical generator as in claim 2, wherein said at least one waveform adjustment signal includes data for setting the output crest factor and output power of the at least one waveform to the values provided by the at least one data structure.

4. An electrosurgical generator as in claim 2, wherein said at least one data structure includes at least one look-up table.

5. An electrosurgical generator as in claim 1, wherein said at least one waveform adjustment signal includes data to alter at least one of the positive peak and the RMS value of the at least one waveform generated by the waveform generator in accordance with the following formula: $CF=V_{PEAK}/V_{RMS}$, where $V_{PEAK}$ is the positive peak of the at least one waveform and $V_{RMS}$ is the RMS value of the at least one waveform.

6. An electrosurgical generator as in claim 1, wherein said at least one waveform adjustment signal includes data to alter at least one of the duty cycle, the positive peak value, and the RMS value of the at least one waveform generated by the waveform generator.

7. An electrosurgical generator as in claim 1, wherein said processing unit executes the set of programmable instructions automatically, in real time and continuously during electrosurgical activation.

8. An electrosurgical generator as in claim 1, further comprising at least one control for manually selecting a value for the output crest factor of the at least one waveform.

9. A method for varying both the output crest factor and output power of at least one waveform generated by an electrosurgical generator based on the changing impedance of tissue during electrosurgery, said method comprising the steps of:
   determining tissue impedance using an output voltage and an output current of the at least one waveform of the electro surgical generator; and
   altering the duty cycle of the at least one waveform to adjust the output crest factor and output power of the at least one waveform generated by said electrosurgical generator based on the determined tissue impedance, wherein said at least one waveform adjustment signal includes data to alter the duty cycle of the at least one waveform generated by the waveform generator in accordance with the following formula: $CF=[(1-D)/D]^{1/2}$, wherein D is the duty cycle and CF is the crest factor of the generated waveform.

10. A method as in claim 9, wherein said adjusting step comprises the step of determining a corresponding output crest factor value and output power value of the at least one waveform for the determined tissue impedance by accessing at least one data structure.

11. A method as in claim 10, wherein said adjusting step comprises the step of setting the output crest factor and output power of the at least one waveform to the values provided by the at least one data structure.

12. A method as in claim 10, wherein said at least one data structure includes at least one look-up table.

13. A method as in claim 9, wherein said adjusting step comprises the step of sending a signal to a waveform generator of said electrosurgical generator to alter at least one of the positive peak and the RMS value of the at least one waveform generated by the waveform generator in accordance with the following formula: $CF=V_{PEAK}/V_{RMS}$, where $V_{PEAK}$ is the positive peak of the generated waveform and $V_{RMS}$ is the RMS value of the at least one waveform.

14. A method as in claim 9, wherein said adjusting step comprises the step of sending at least one signal to a waveform generator of said electrosurgical generator to alter at least one of the duty cycle, the positive peak value, and the RMS value of the at least one waveform generated by the waveform generator.

15. A method as in claim 9, further comprising the step of manually selecting a value for the output crest factor and a value for the output power of the at least one waveform.

16. A method as in claim 9, wherein said method is performed automatically, in real time and continuously for the duration of the electro surgery.

17. An electrosurgical generator capable of varying both the output crest factor and output power of at least one waveform based on the changing impedance of tissue during electrosurgery, said electrosurgical generator comprising:
   means for determining tissue impedance using an output voltage and output current of the at least one waveform generated by the electrosurgical generator; and
   means for altering the duty cycle of the at least one waveform to adjust the output crest factor and output power of the at least one waveform generated by said electrosurgical generator based on the determined tissue impedance, wherein said at least one waveform adjustment signal includes data to alter the duty cycle of the at least one waveform generated by the waveform generator in accordance with the following formula: $CF=[(1-D)/D]^{1/2}$, wherein D is the duty cycle and CF is the crest factor of the generated waveform.

18. A power source for generating an output voltage and an output current for an electrosurgical generator system, said electrosurgical system is capable of varying both the output crest factor and output power of at least one waveform based on the changing impedance of tissue during electrosurgery, and said electrosurgical system including a processing unit for receiving at least one signal indicative of the output voltage and the output current of the at least one waveform, said processing unit executing a set of programmable instructions for determining the tissue impedance using the output voltage and output current of the at least one waveform and transmitting at least one waveform adjustment signal; said electrosurgical system further including a waveform generator for receiving the at least one waveform adjustment signal for altering the duty cycle of the at least one waveform to adjust the output crest factor and output power of the at least one waveform based on the determined tissue impedance, wherein said at least one waveform adjustment signal includes data to alter the duty cycle of the at least one waveform generated by the waveform generator in accordance with the following formula: $CF=[(1-D)/D]^{1/2}$, wherein D is the duty cycle and CF is the crest factor of the generated waveform.

* * * * *